United States Patent [19]

Weinberger

[11] Plant 4,942

[45] Nov. 16, 1982

[54] NECTARINE TREE (87-101)

[75] Inventor: John H. Weinberger, Fresno, Calif.

[73] Assignee: Superior Farming Company, Bakersfield, Calif.

[21] Appl. No.: 282,927

[22] Filed: Jul. 13, 1981

[51] Int. Cl.[3] ..... A01H 5/03

[52] U.S. Cl. ..... Plt./41

[58] Field of Search ..... Plt./41

*Primary Examiner*—Robert E. Bagwill

*Attorney, Agent, or Firm*—Roger B. Webster

[57] ABSTRACT

A nectarine tree which is of medium size, medium vigor, upright-spreading, dense, and round-topped; foliated with medium size, ovate, lanceolate, acutely pointed leaves of smooth texture and medium thickness, the leaves having a crenate margin, a petiole medium in length and thickness, and irregularly alternate, medium size, green, reniform glands positioned on the petiole and the base of the blade; flowers from buds which are of medium size and length, plump, appressed, and pubescent; the flowers, of medium season, being large and pink; and is a regular and productive bearer of medium size, uniform, symmetrical, slightly ovate, freestone fruit having yellow skin substantially overspread with red, yellow, reddish-tinged flesh streaked with red next to the stone, and a brown stone.

1 Drawing Figure

BACKGROUND OF THE VARIETY

1. Field of the Invention

In the conduct of an extensive plant breeding program—on behalf of a commercial farming company, and in such company's experimental orchard located near Fresno, Fresno County, Calif.—I have originated a substantial number of new and distinct varieties of fruit trees, and which include the present variety of nectarine tree.

2. Classification of the Variety

The present variety of nectarine tree is embraced by Class 41, Plants, of the U.S. Patent Office Manual of Classification.

3. Prior Varieties

Among existing varieties of nectarine trees which are known to me, and mentioned herein, are the Summer Grand (U.S. Plant Pat. No. 2,879) and the Fantasia (unpatented).

ORIGIN OF THE VARIETY

The present variety of nectarine tree was originated by me as an open-pollinated seedling of an unidentified, late ripening, seedling nectarine tree. A number of such open-pollinated seedlings were grown to fruition, in the aforesaid experimental orchard, under careful and continuing observation by me; the present variety being a selection of one of such open-pollinated seedlings.

ASEXUAL REPRODUCTION OF THE VARIETY

Asexual reproduction of the variety was successfully accomplished, under my direction and in the aforesaid experimental orchard, by budding; such asexual reproductions, in maturity, having run true to the original tree in all respects.

SUMMARY OF THE VARIETY

The present variety of nectarine tree is, characteristically, of medium size, medium vigor, upright-spreading, dense, and round-topped; foliated with medium size, ovate, lanceolate, acutely pointed leaves of smooth texture and medium thickness, the leaves having a crenate margin, a petiole medium in length and thickness, and irregularly alternate, medium size, green, reniform glands positioned on the petiole and the base of the blade; flowers from buds which are of medium size and length, plump, appressed, and pubescent; the flowers, of medium season, being large and pink; and is a regular and productive bearer of medium size, uniform, symmetrical, slightly ovate, freestone fruit having yellow skin substantially overspread with red, yellow, reddish-tinged flesh streaked with red next to the stone, and a brown stone.

The present variety of nectarine tree is further, and more particularly, characterized by fruit which, in comparison to the fruit of the Summer Grand, ripens about a week later.

The present variety of nectarine tree is still further characterized by fruit which, in comparison with the fruit of the Summer Grand, has a suture less depressed and the apex more depressed; by smoother and more highly colored skin having less speckling; and by a base less flat and broad.

The present variety of nectarine tree is still further characterized by fruit which, in comparison to the Fantasia, has a more depressed apex, is less globose and more ovate, and is more highly colored but smaller in size.

BRIEF DESCRIPTION OF THE DRAWING

The drawing is an illustration, by photographic reproduction in color, of separate fruit of the variety and a twig with leaves; one fruit being cut into halves, with the stone remaining in one half.

DESCRIPTION OF THE VARIETY

The botanical details of this new and distinct variety of nectarine tree—with color definitions (except those in common color terms) referenced to Plochere Color System (in book form)—are as follows:

Tree:

*Size.*—Medium.
*Vigor.*—Medium.
*Growth.*—Upright-spreading.
*Density.*—Dense.
*Form.*—Round-topped.

*Production.*—Productive.
*Bearing.*—Regular bearer.

Trunk:
*Size.*—Medium.
*Texture.*—Medium.

Branches:
*Size.*—Medium.
*Texture.*—Medium.
*Color.*—New wood — Green, dull. Mature wood — Brown.

Leaves:
*Size.*—Medium. Average length — 16.7 cm. Average width — 4.0 cm.
*Form.*—Ovate. Lanceolate. Acutely pointed.
*Thickness.*—Medium.
*Color.*—Medium green.
*Texture.*—Smooth.
*Margin.*—Crenate.
*Petiole.*—Medium length. Medium thickness.
*Glands.*—Number — 3–4. Alternate — irregular. Medium size. Reniform. Green. Positioned distal on petiole and basal on blade.
*Stipules.*—Shed as leaves mature.

Flower buds:
*Size.*—Medium.
*Length.*—Medium.
*Form.*—Plump. Appressed. Pubescent.

Flowers:
*Date of full bloom.*—Mar. 7, 1980. Medium, as compared with other varieties.
*Size.*—Large.
*Color.*—Pink.

Fruit:
*Maturity when described.*—Firm ripe — July 23, 1980.
*Date of first picking.*—July 22, 1980.
*Date of last picking.*—Aug. 1, 1980.
*Size.*—Uniform. Medium. Average diameter axially — 70 mm. Average transversely in suture plane — 65 mm.
*Form.*—Uniform. Symmetrical. Slightly ovate.
*Suture.*—A shallow, inconspicuous line extending from base to beyond apex, with slight depression beyond pistil point.
*Ventral surface.*—Rounded. Lipped toward apex.
*Lips.*—Equal.
*Cavity.*—Rounded. Elongated in suture plane, with suture showing on one side. Average depth — 10 mm. Average breadth — 18 mm.
*Markings.*—None.
*Base.*—Rounded.
*Apex.*—Depressed.
*Pistil point.*—Apical.

Skin:
*Thickness.*—Medium.
*Texture.*—Medium.
*Tenacity.*—Tenacious to flesh.
*Tendency to crack.*—None in dry season.
*Color.*—Ground Color — Yellow. Blush Color — Red (Plate 17 — No. 385 — Crimson Glory).
*Down.*—Wanting.

Flesh:
*Color.*—Yellow (Plate 7 — No. 147 — Nasturtium), with reddish tinge, and streaked with red next to stone.
*Surface of pit cavity.*—Red.
*Amygdalin.*—Wanting.
*Juice.*—Moderate.
*Texture.*—Medium. Fine. Melting.
*Fibers.*—Few. Fine. Tender.
*Ripens.*—Evenly.
*Flavor.*—Acid. Delicate.
*Aroma.*—Distinct.
*Eating quality.*—Best.

Stone:
*Type.*—Free. Adheres to flesh slightly along dorsal edge.
*Fibers.*—Short. Parts from flesh smoothly.
*Size.*—Medium. Average length — 40 mm. Average breadth — 28 mm. Average thickness — 20 mm.
*Form.*—Obovoid.
*Base.*—Straight.
*Hilum.*—Oval.
*Apex.*—Rounded. Acuminate.
*Sides.*—Equal.
*Surface.*—Regularly furrowed toward apex. Ridged toward apex. Pitted from base to above center.
*Ridges.*—Rounded.
*Pits.*—Elongated.
*Ventral edge.*—Thin, with wing throughout.
*Dorsal edge.*—Full, with shallow groove throughout.
*Color.*—Brown (Plate 14 — No. 313 — Congo).
*Tendency to split.*—Slight in dry season.

Use: Market.
Keeping quality: Good.
Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, particularly characterized by freestone fruit in harvest about one week later than the fruit of the Summer Grand.

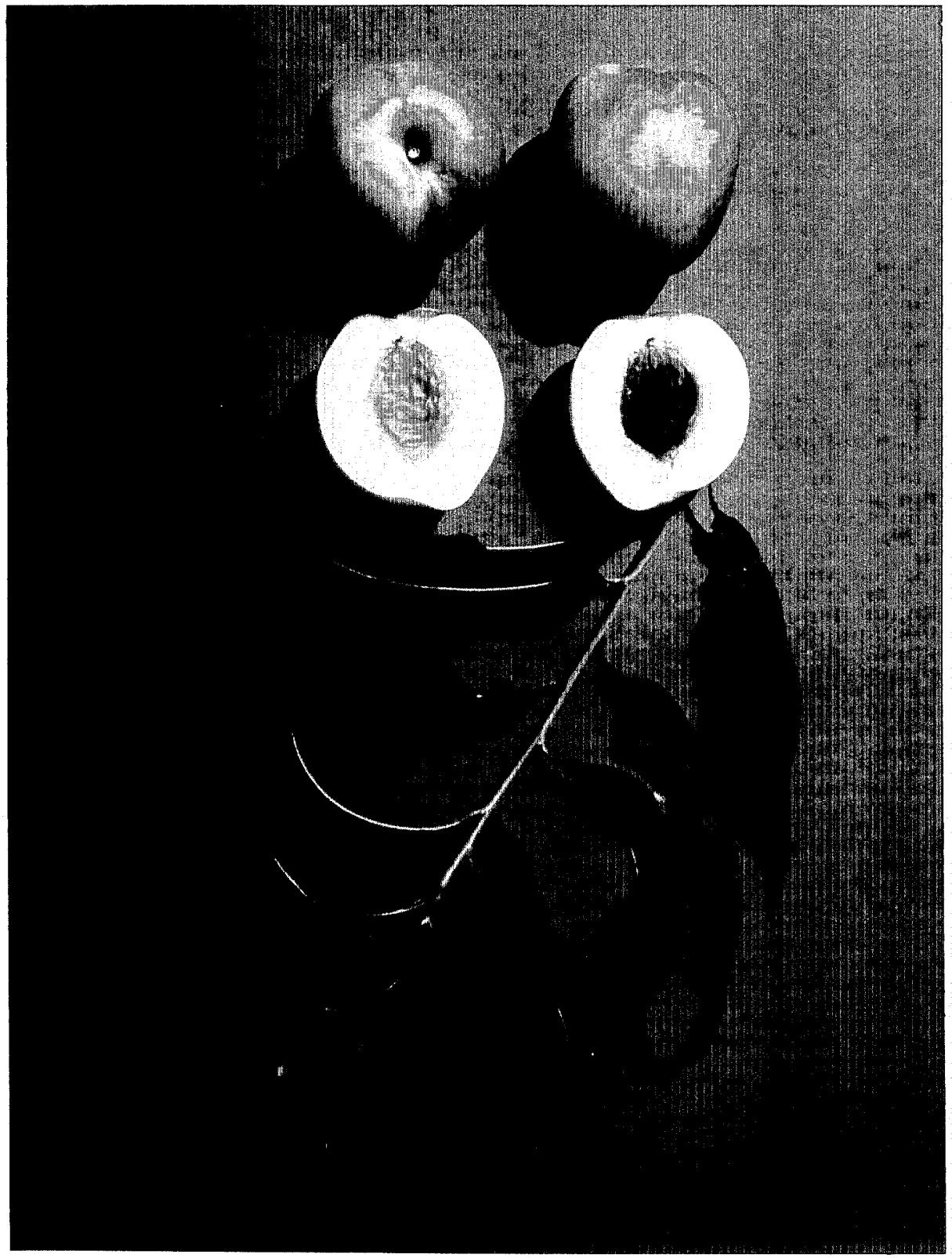

* * * * *